(12) United States Patent
Flores et al.

(10) Patent No.: US 8,926,184 B2
(45) Date of Patent: Jan. 6, 2015

(54) FLUID BEARING WITH NON-UNIFORM GROOVES

(71) Applicant: Seagate Technology LLC, Cupertino, CA (US)

(72) Inventors: Paco Gregor Flores, Felton, CA (US); Lynn Bich-Quy Le, San Jose, CA (US)

(73) Assignee: Seagate Technology LLC, Cupertino, CA (US)

( * ) Notice: Subject to any disclaimer, the term of this patent is extended or adjusted under 35 U.S.C. 154(b) by 96 days.

(21) Appl. No.: 13/787,667

(22) Filed: Mar. 6, 2013

(65) Prior Publication Data

US 2014/0140644 A1    May 22, 2014

Related U.S. Application Data

(60) Provisional application No. 61/729,387, filed on Nov. 22, 2012.

(51) Int. Cl.
  *F16C 32/06* (2006.01)
  *C12N 15/85* (2006.01)
  *C12P 21/00* (2006.01)

(52) U.S. Cl.
  CPC ............ *C12N 15/85* (2013.01); *F16C 32/0666* (2013.01); *F16C 32/0629* (2013.01); *C12P 21/00* (2013.01)
  USPC ............ 384/115; 384/100; 384/107; 384/123

(58) Field of Classification Search
  USPC ................. 384/100, 107, 112–115, 120, 123, 384/290–293; 320/67 R, 90
  See application file for complete search history.

(56) References Cited

U.S. PATENT DOCUMENTS

| | | | |
|---|---|---|---|
| 3,386,783 A * | 6/1968 | Scheufler ...................... | 384/291 |
| 5,180,173 A * | 1/1993 | Kimura et al. ................ | 277/400 |
| 6,350,059 B1 | 2/2002 | Takahashi | |
| 6,358,394 B1 * | 3/2002 | Cochran ....................... | 205/640 |
| 6,527,625 B1 * | 3/2003 | Kajiwara et al. ................ | 451/41 |
| 6,540,590 B1 * | 4/2003 | Kajiwara et al. ................ | 451/41 |
| 6,838,795 B2 * | 1/2005 | Kloeppel et al. .............. | 384/112 |
| 6,877,902 B2 | 4/2005 | Ikegawa | |
| 7,235,168 B2 * | 6/2007 | Heine et al. ................... | 205/640 |
| 7,441,957 B2 | 10/2008 | Hong et al. | |
| 7,465,098 B2 | 12/2008 | Hendriks et al. | |
| 7,637,663 B2 * | 12/2009 | Hendriks et al. .............. | 384/107 |
| 7,663,278 B2 | 2/2010 | Hendriks et al. | |
| 7,837,390 B2 | 11/2010 | Kusaka et al. | |
| 7,976,221 B2 | 7/2011 | Huang et al. | |
| 2002/0134683 A1 * | 9/2002 | Steele .......................... | 204/640 |
| 2003/0205943 A1 * | 11/2003 | Kloeppel et al. ................ | 310/90 |
| 2003/0221973 A1 * | 12/2003 | Heine et al. ................... | 205/656 |
| 2007/0215458 A1 * | 9/2007 | Parkhomovsky et al. .... | 204/224 M |
| 2007/0292058 A1 * | 12/2007 | Hendriks et al. .............. | 384/100 |

* cited by examiner

*Primary Examiner* — Marcus Charles (57) ABSTRACT

Provided herein is an apparatus, including a fluid dynamic bearing, wherein the fluid dynamic bearing includes a set of pressure-generating grooves, and wherein the set of pressure-generating grooves includes a plurality of chevron-shaped grooves, each chevron-shaped groove including at least two selected from a non-uniform depth, non-uniform angle, a non-uniform width, or a non-uniform length, selected to provide a predetermined spindle-motor stiffness to the journal bearing during steady-state operation and during a shock event.

22 Claims, 7 Drawing Sheets

ND GROOVES

CROSS-REFERENCE TO RELATED APPLICATIONS

This application claims the benefit of U.S. Provisional Patent Application No. 61/729,387, filed Nov. 22, 2012.

BACKGROUND

Fluid dynamic bearings are utilized in motors used for computer hard drives, and fluid dynamic bearings are designed to provide stiffness to the motors in which they are used. Such bearings use a fluid medium between two of the bearing surfaces to provide stiffness. In operation, a groove-bearing surface of a fluid dynamic bearing pumps the fluid medium as a response to the relative motion between two bearing surfaces, and, consequently pressurizes the bearing, providing stiffness.

In a journal bearing, radial motion and angular motion are resisted by the bearing as a result of the stiffness provided. In a thrust bearing, axial and angular motion are resisted as a result of the stiffness provided. In either case, a groove-bearing surface and bearing gap (the offset between bearing surfaces) may be adjusted for stiffness. As such, different groove configurations may be used in different bearing designs.

SUMMARY

Provided herein is an apparatus, including a fluid dynamic bearing, wherein the fluid dynamic bearing includes a set of pressure-generating grooves, and wherein the set of pressure-generating grooves includes a plurality of chevron-shaped grooves, each chevron-shaped groove including at least two selected from a non-uniform depth, non-uniform angle, a non-uniform width, or a non-uniform length, selected to provide a predetermined spindle-motor stiffness to the journal bearing during steady-state operation and during a shock event.

These and other features, aspects, and advantages may be better understood with reference to the following drawings, description, and appended claims.

DESCRIPTION

It should be understood by persons having ordinary skill in the art that particular embodiments described and/or illustrated herein may vary, as elements in such embodiments may vary. It should likewise be understood that a particular embodiment described and/or illustrated herein has elements which may be readily separated from the particular embodiment and optionally combined with any of several other embodiments or substituted for elements in any of several other embodiments described herein.

It should also be understood by persons having ordinary skill in the art that the terminology used herein is for the purpose of describing particular embodiments, and the terminology is not intended to be limiting. Unless indicated otherwise, ordinal numbers (e.g., first, second, third, etc.) are used to distinguish or identify different elements or steps in a group of elements or steps, and do not supply a serial or numerical limitation on the elements or steps. For example, "first," "second," and "third" elements or steps need not necessarily appear in that order, and recitation of "first," "second," and "third" elements or steps need not necessarily be limited to three elements or steps recited. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

Unless defined otherwise, all technical and scientific terms used herein have the same meaning as commonly understood by persons of ordinary skill in the art.

Some embodiments will now be described in greater detail.

Figure 1:
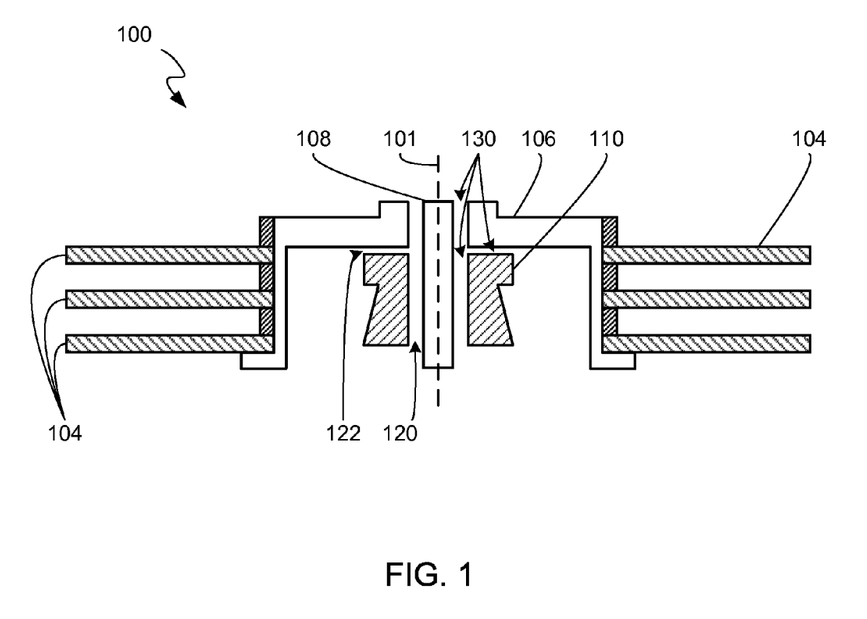
FIG. 1 provides a cross-sectional view of a fluid dynamic bearing motor in an embodiment.
Figure 9:
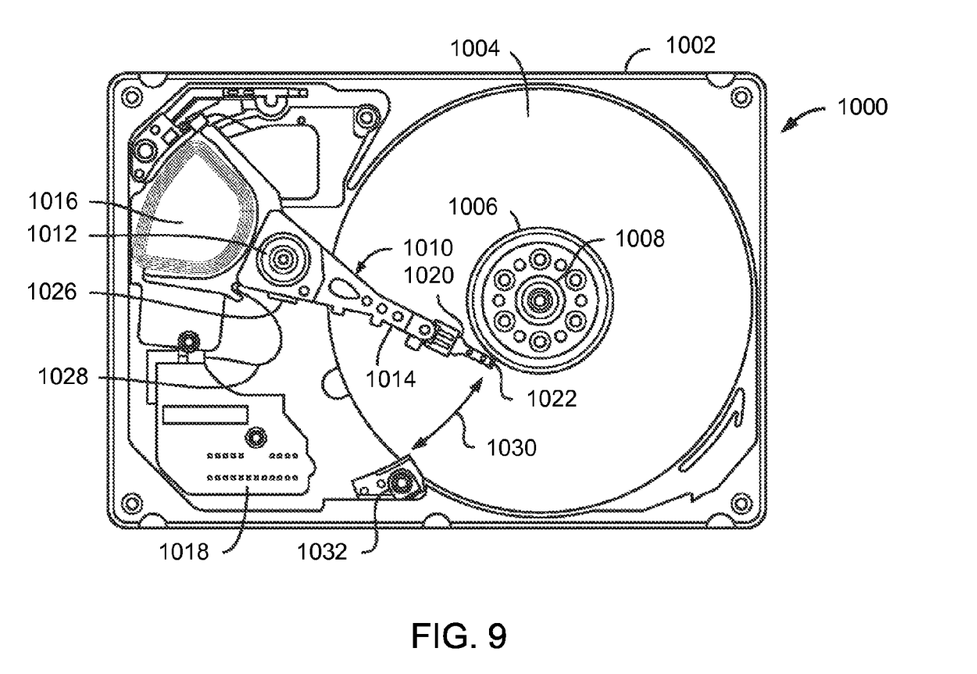
FIG. 9 provides a plan view of a data storage device in an embodiment.

FIG. 1 is a cross-sectional view of a fluid dynamic bearing motor 100, according to an embodiment of the present invention. The fluid dynamic bearing motor 100 may be used in the disk drive 1000 (FIG. 9). For example, data storage disks 104 may correspond to the data storage disks 1004 (FIG. 9).

The fluid dynamic bearing motor 100 may reduce wear by reducing friction while maintaining the alignment between a hub 106, a shaft 108, and/or a sleeve 110. The data storage disks 104 may be supported and rotated by the fluid dynamic bearing motor 100 about a centerline axis 101.

The data storage disks 104 may be rotated at high speeds during operation using magnets (not shown) and a stator (not shown). Magnets, for example mounted on the hub 106 may interact with the stator to cause rotation of the hub 106 relative to the stator. The magnets may be formed as a unitary annular ring or may be formed as a plurality of individual magnets that are spaced about the periphery of the hub. The magnets may be magnetized to form two or more magnetic poles.

Figure 2:
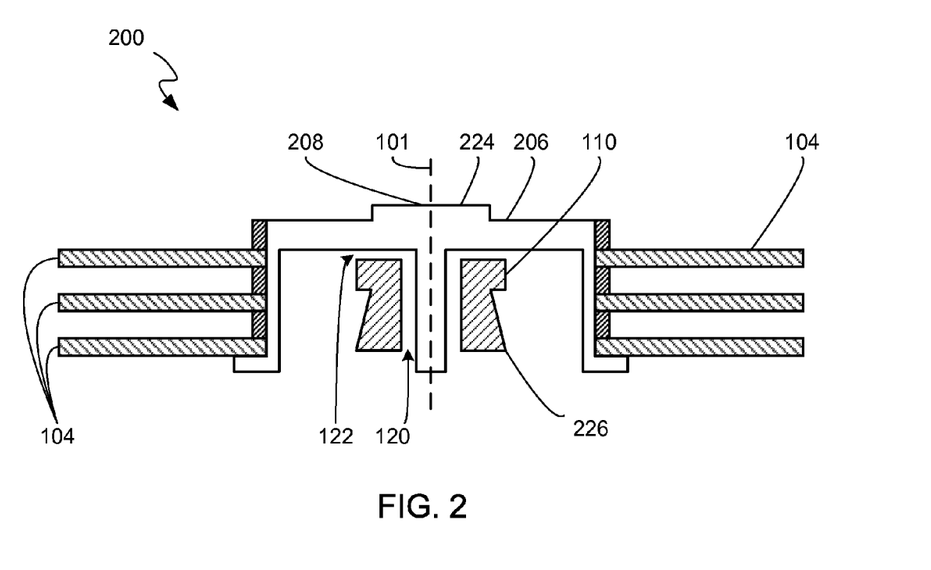
FIG. 2 provides a cross-sectional view of a fluid dynamic bearing motor with a coupled hub portion and shaft portion in an embodiment.
Figure 3:
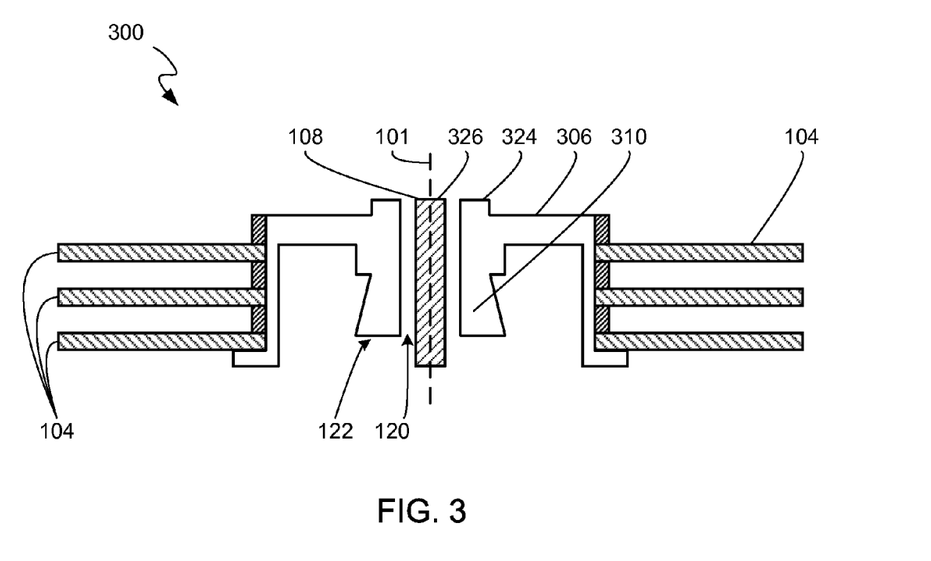
FIG. 3 provides a cross-sectional view of a fluid dynamic bearing motor with a coupled hub portion and sleeve portion in an embodiment.

The fluid dynamic bearing motor 100 includes a stationary component and a rotatable component. The rotatable component rotates relative to the stationary component and defines a fluid dynamic journal bearing 120 and a thrust bearing 122 therebetween. FIG. 2 and FIG. 3 illustrate various examples of stationary components and rotatable components, according to embodiments of the present invention.

FIG. 2 is a cross-sectional view of a fluid dynamic bearing motor 200 with a rotatable component 224 and a stationary component 226, according to an embodiment of the present invention. In one embodiment, the rotatable component 224 may include a hub portion 206 and a shaft portion 208 while the stationary component 226 includes the sleeve 110. For example, the hub portion 206 and shaft portion 208 may be coupled with one another to form a single unitary piece, such that they rotate together about the centerline axis 101. Alternatively, the hub portion 206 and the shaft portion 208 may be originally formed from a single piece of material. The interface between the shaft portion 208 and the sleeve 110 may define the fluid dynamic journal bearing 120 while the interface between the hub portion 206 and the sleeve 110 may define the thrust bearing 122. According to some embodiments, the shaft portion 208 supports the hub portion 206.

FIG. 3 is a cross-sectional view of a fluid dynamic bearing motor 300 with a rotatable component 324 and a stationary component 326, according to an embodiment of the present invention. In one embodiment, the rotatable component 324 may include a hub portion 306 and a sleeve portion 310 while the stationary component 326 includes the shaft 108. For example, the hub portion 306 and sleeve portion 310 may be coupled with one another to form a single unitary piece, such that they rotate together about the centerline axis 101. Alternatively, the hub portion 306 and the sleeve portion 310 may originally be formed from a single piece of material. The interface between the hub portion 306 and the shaft 108 and/or the interface between the sleeve portion 310 and shaft 108 may define a fluid dynamic journal bearing 120. In addition, the thrust bearing 122 may be disposed underneath the sleeve portion 310 or above (not shown) the hub portion 306.

Returning to FIG. 1, in some embodiments, a fluid (e.g., a lubricating oil, a ferromagnetic fluid, etc.), fills the journal bearing 120, the thrust bearing 122, and/or interfacial regions 130 between the hub 106, the shaft 108, and/or the sleeve 110 as well as between other stationary and rotatable components (not shown). It is appreciated that the lubricating fluid described herein is exemplary and not intended to limit the scope of the embodiments of the present invention. For example, the fluid may include a lubricating liquid, a lubricating gas, or a combination of a lubricating liquid and lubricating gas.

As described in more detail herein below, the shaft 108 and/or the sleeve 110 of FIG. 1 may include pressure-generating grooves (not shown). It should be understood, especially in view of the additional detail below, that the pressure-generating grooves may include asymmetric grooves and/or symmetric grooves. The asymmetric grooves and/or the symmetric grooves, in addition to the chevron-shaped grooves provided herein below, may have additional pattern elements including, for example, herringbone and/or sinusoidal pattern elements. The pressure-generating grooves may, for example, induce fluid flow in the interfacial regions 130 in order to generate a localized region of dynamic high pressure and radial stiffness during rotation of the shaft 108.

Figure 4A:
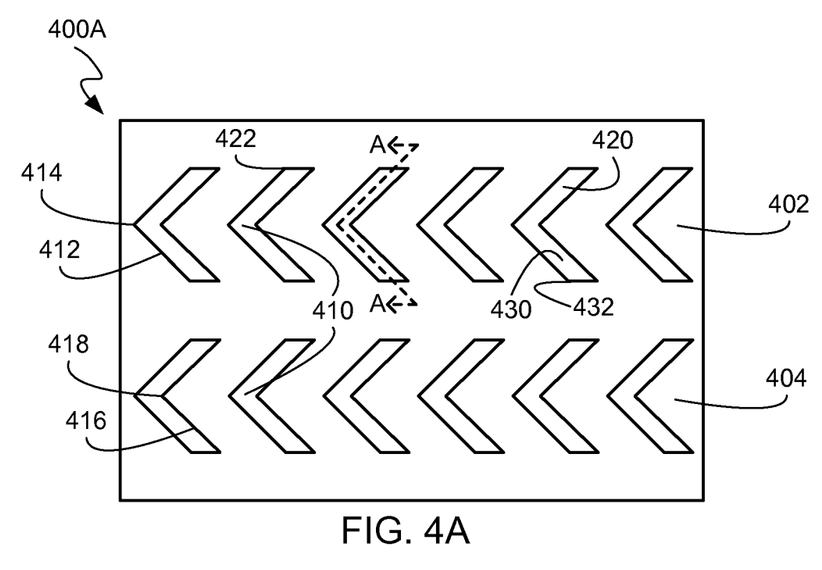
FIG. 4A provides an embodiment of a journal bearing sleeve or shaft, unrolled to provide a two-dimensional view of the grooves thereon.

FIG. 4A illustrates a journal bearing sleeve or shaft, unrolled to provide a two-dimensional view of the grooves (e.g., chevron-shaped grooves) thereon. As shown, unrolled sleeve or shaft 400A may comprise a double journal bearing comprising an upper journal bearing 402 and a lower journal bearing 404, each with grooves 410 thereon. Such grooves may be described as upper journal bearing grooves and lower journal bearing grooves of a double journal bearing, which double journal bearing more effectively utilizes a given bearing span than a single journal bearing (e.g., sleeve or shaft comprising a single set of chevron-shaped grooves) by concentrating the restorative forces provided by the ends of the upper and lower journal bearing grooves, therefore providing a greater angular force (e.g., to counter angular displacement of the shaft). In addition, as described herein, having shallower grooves at the ends of the upper and lower journal bearing grooves, where the groove depth and journal gap may go to zero, makes the double journal bearing even more effective. Each of grooves 410 comprises an outside wall 412 with an outside wall vertex 414 and an inside wall 416 with inside wall vertex 418. Each of grooves 410 also comprises a first segment 420 extending from vertices 414 and 418 to a first terminus 422, wherein the first segment 420 and/or the first terminus 422 may be oriented toward an end of bearing (e.g., top/bottom of journal bearing). And each of grooves 410 also comprises a second segment 430 extending from vertices 414 and 418 to a second terminus 432, wherein the second segment 430 and/or the second terminus 432 may be oriented toward a center/middle of the bearing (e.g., center/middle of journal bearing). It should be understood that, while FIG. 4A provides a sleeve or a shaft with grooves (e.g., chevron-shaped grooves oriented such that the vertices point in the direction of rotation of the sleeve or shaft) thereon, embodiments are not limited to one of the sleeve or the shaft comprising grooves. In some embodiments, for example, each of the sleeve and the shaft have grooves thereon, matched to provide a pressure-generating system optimized for normal and aberrant (e.g., under an applied load) function.

Figure 4B:
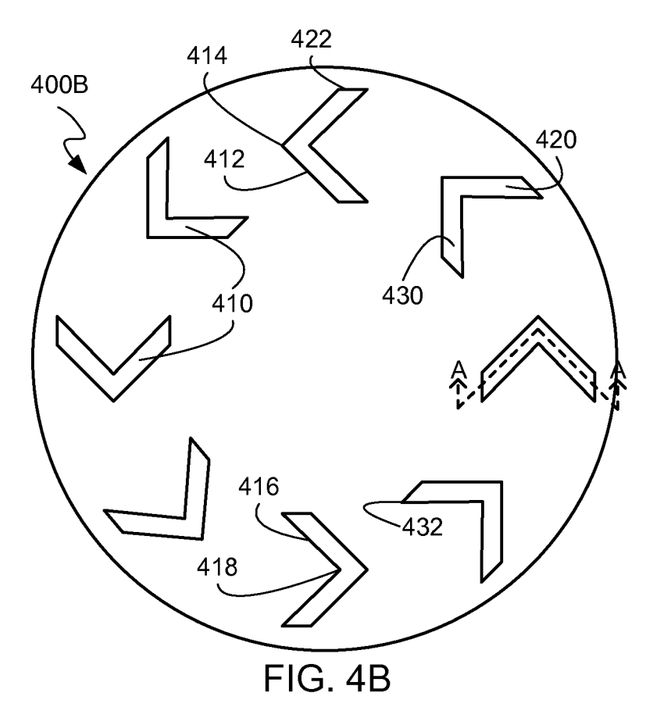
FIG. 4B provides a two-dimensional view of an embodiment of a thrust bearing with grooves thereon.

Likewise, FIG. 4B provides a two-dimensional view of a thrust surface of a thrust bearing with grooves thereon (e.g., chevron-shaped grooves), which thrust bearing may represent either a top or bottom thrust bearing in an assembly. As shown, thrust surface 400B, which may be either the top or bottom surface of a thrust bearing, may have grooves 410 thereon. Each of grooves 410 comprises an outside wall 412 with an outside wall vertex 414 and an inside wall 416 with inside wall vertex 418. Each of grooves 410 also comprises a first segment 420 extending from vertices 414 and 418 to a first terminus 422, wherein the first segment 420 and/or the first terminus 422 may be oriented toward an end of bearing (e.g., circumferential edge of thrust bearing). And each of grooves 410 also comprises a second segment 430 extending from vertices 414 and 418 to a second terminus 432, wherein the second segment 430 and/or the second terminus 432 may be oriented toward a center/middle of the bearing (e.g., center/middle of thrust bearing). It should be understood that, while FIG. 4B provides a thrust surface with grooves (e.g., chevron-shaped grooves oriented such that the vertices point in the direction of rotation of the sleeve or shaft) thereon, embodiments are not limited to one of the thrust surface or the opposing surface comprising grooves. In some embodiments, for example, each of the thrust surface and the opposing surface have grooves thereon, matched to provide a pressure-generating system optimized for normal and aberrant (e.g., under an applied load) function.

A groove profile may be designed for a pressure for a given bearing gap during steady-state operation, which steady-state operation includes operation at a substantially constant temperature (e.g., 30-40° C., such as 30-35° C. or 35-40° C.) and substantially constant rotation (e.g., 7200 RPM [spindle speed]). With respect to a journal bearing, for example, the given bearing gap is the nominal gap for the sleeve and shaft in the upright, vertical spin axis ("VSA") condition. When a radial load is applied, for example, during a shock event (e.g., dropping disk drive 1000 of FIG. 10), an opposing force is generated by the grooves acting on the fluid between the bearing surfaces, which opposing force acts to prevent or mitigate further displacement of the shaft. In the case of vibration, where the applied load may be relatively small, the bearing gap does not change much; however, in the case of a large load, the bearing gap, at the bearing ends, may close, even to the point of contact between the bearing surfaces. The following groove profiles discussed with respect to FIGS. 5A-5F and 6-8 may have, for example, shallower groove depths at the bearing ends to generate stronger resistive (or restoring) forces, for example, when loads are applied. In addition, such groove profiles may be used to generate stronger resistive (or restoring) forces, for example, during operation at a higher temperature than one in an optimum temperature range, at which higher temperature smaller bearing gaps may occur (e.g., journal bearing in the horizontal spin axis ("HSA") condition; top and/or bottom thrust bearing) due to lesser fluid viscosity. A temperature in an optimum temperature range is a temperature between about 35° C. and 45° C., with a normal temperature range being between about 5° C. and 60° C. A higher temperature than one in an optimum temperature range includes a temperature in the normal temperature range such as a temperature >45° C., such as >50° C., for example, >55° C. A higher temperature than one in an optimum temperature range further includes a temperature greater than one in the normal temperature range such as a temperature >60° C., such as >65° C., for example, >70° C.

Each of FIG. 5A, FIG. 5B, FIG. 5C, FIG. 5D, FIG. 5E, and FIG. 5F provide a different lengthwise view (Section A-A of FIGS. 4A and/or 4B) of a pressure-generating groove of a fluid dynamic bearing (e.g., journal bearing, thrust bearing). Such lengthwise views provide different depth profiles. While each depth profile described herein below with reference to FIG. 5A, FIG. 5B, FIG. 5C, FIG. 5D, FIG. 5E, and FIG. 5F is primarily described with respect to non-uniform depth along groove length, it should be understood that groove length, groove width, and certain groove angles may vary with the depth as well, as described herein.

Figure 5A:
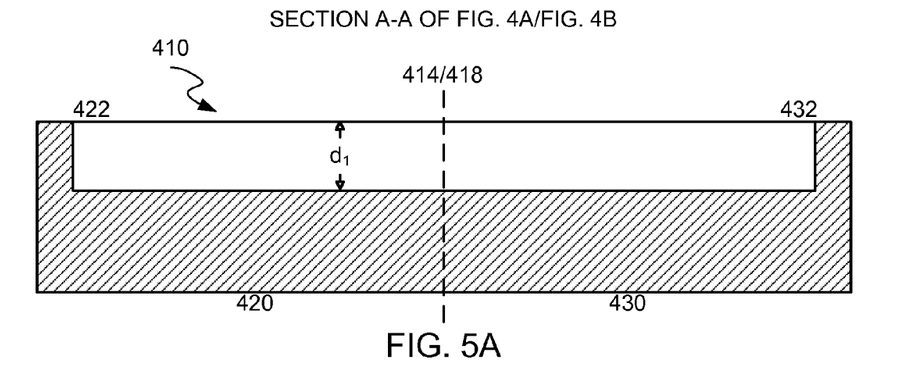
FIG. 5A, FIG. 5B, FIG. 5C, FIG. 5D, FIG. 5E, and FIG. 5F each provide a lengthwise view of a different groove-depth profile.

FIG. 5A provides a groove having a uniform depth profile when viewed along the length of the groove from the first terminus 422 to the second terminus 432 (see Section A-A in FIGS. 4A, 4B). As shown, the groove may have a depth $d_1$ along its entire length; that is, the groove may have a depth $d_1$ at the first terminus 422, a depth $d_1$ along the first segment 420, a depth $d_1$ at vertices 414 and 418, a depth $d_1$ along the second segment 430, and a depth $d_1$ at the second terminus 432, wherein the depth $d_1$ is described herein below.

Figure 5B:
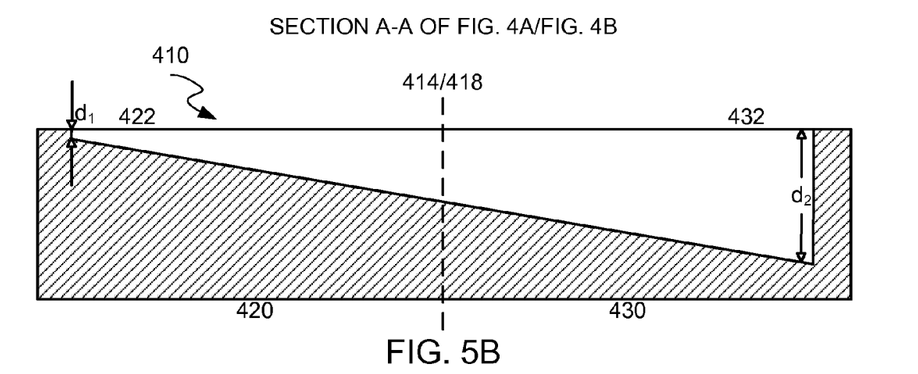

FIG. 5B provides a groove having a non-uniform depth profile when viewed along the length of the groove from the first terminus 422 to the second terminus 432 (see Section A-A in FIGS. 4A, 4B). As shown, the groove may have a depth $d_1$ at the first terminus 422 and a depth $d_2$ at the second terminus 432, wherein the depth $d_1$ and the depth $d_2$ are described herein below. The depth of the groove at any point along the length of the groove profiled in FIG. 5B may be determined from the slope calculated from the depth $d_1$ at the first terminus 422 and the depth $d_2$ at the second terminus 432. As such, the groove of FIG. 5B may have a non-uniform depth along its length, having a relatively shallow depth $d_1$ at the first terminus 422, an increasing depth along the first segment 420, vertices 414 and 418, and the second segment 430, and a relatively deep depth $d_2$ at the second terminus 432.

Figure 5C:
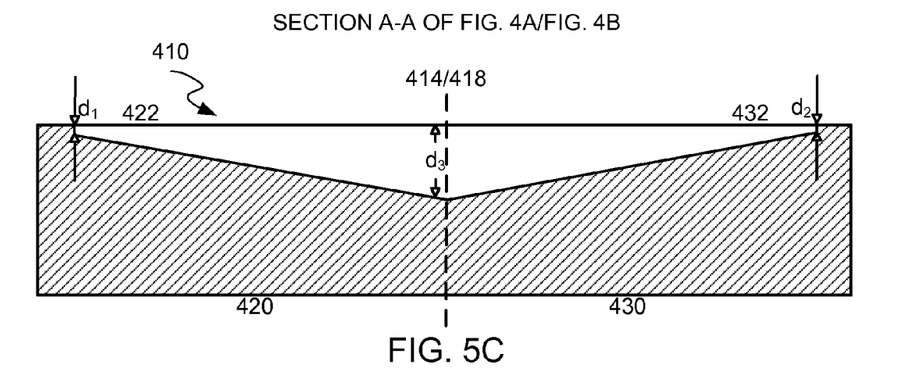

FIG. 5C provides a groove having a non-uniform depth profile when viewed along the length of the groove from the first terminus 422 to the second terminus 432 (see Section A-A in FIGS. 4A, 4B). As shown, the groove may have a depth $d_1$ at the first terminus 422, a depth $d_2$ at the second terminus 432, and a depth $d_3$ at the vertices 414 and 418, wherein the depths $d_1$, $d_2$, and $d_3$ are described herein below. The depth of the groove at any point along the first segment 420 of the groove profiled in FIG. 5C may be determined from the slope calculated from the depth $d_1$ at the first terminus 422 and the depth $d_3$ at the vertices 414 and 418. The depth of the groove at any point along the second segment 430 of the groove profiled in FIG. 5C may be determined from the slope calculated from the depth $d_2$ at the second terminus 432 and the depth $d_3$ at the vertices 414 and 418. While FIG. 5C presents depth $d_1$ and depth $d_2$ as relatively equal, the depth $d_1$ and the depth $d_2$ may be the same or different. When the depth $d_1$ and the depth $d_2$ are different, the depth $d_1$ at the first terminus 422 may be shallower than the depth $d_2$ at the second terminus 432.

Figure 5D:
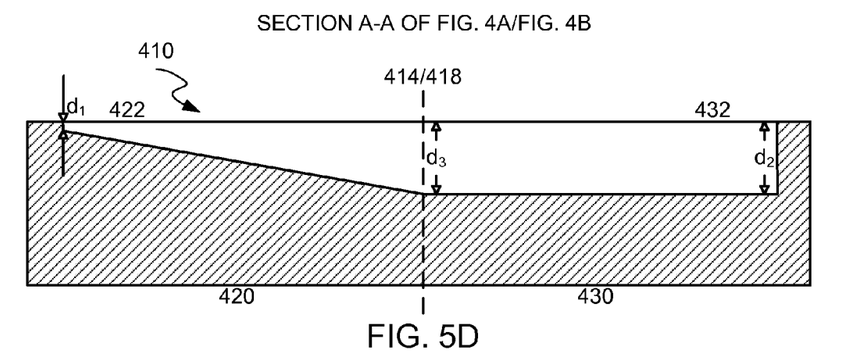

FIG. 5D provides a groove having a non-uniform depth profile when viewed along the length of the groove from the first terminus 422 to the second terminus 432 (see Section A-A in FIGS. 4A, 4B). As shown, the groove may have a depth $d_1$ at the first terminus 422, a depth $d_2$ at the second terminus 432, and a depth $d_3$ at the vertices 414 and 418, wherein the depths $d_1$, $d_2$, and $d_3$ are described herein below. The depth of the groove at any point along the first segment 420 of the groove may be determined from the slope calculated from the depth $d_1$ at the first terminus 422 and the depth $d_3$ at the vertices 414 and 418. The depth of the groove at any point along the second segment 430 of the groove profiled in FIG. 5D may be determined from the slope calculated from the depth $d_2$ at the second terminus 432 and the depth $d_3$ at the vertices 414 and 418. While FIG. 5D presents depth $d_2$ and $d_3$ as relatively equal, the depth $d_2$ and the depth $d_3$ may be the same or different. When the depth $d_2$ and the depth $d_3$ are the same, as shown in FIG. 5D, the groove may have a uniform portion as represented by second segment 430 and a non-uniform portion as represented by first segment 420. When the depth $d_2$ and the depth $d_3$ are different, the depth $d_3$ at vertices 414 and 418 may be shallower than the depth $d_2$ at the second terminus 432. The depth of the groove at any point along the second segment 430 of the groove may be determined from the slope calculated from the depth $d_3$ at the vertices 414 and 418 and the depth $d_2$ at the second terminus 432.

Figure 5E:
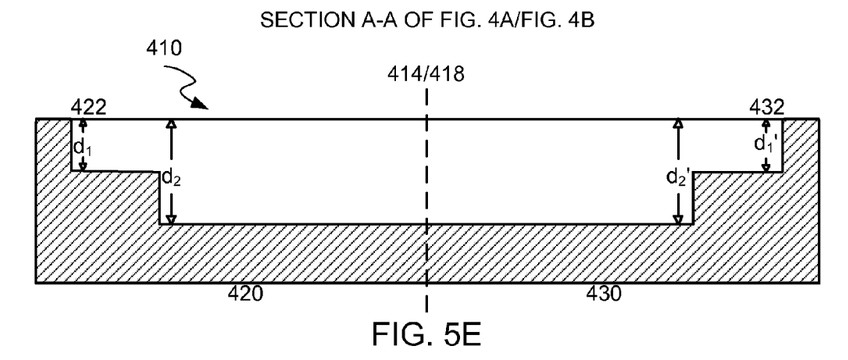

FIG. 5E provides a groove having a non-uniform depth profile when viewed along the length of the groove from the first terminus 422 to the second terminus 432 (see Section A-A in FIGS. 4A, 4B). As shown, the groove may have a depth $d_1$ at the first terminus 422, a depth $d_2$ at a point along the first segment 420, a depth $d_1'$ at the second terminus 432, and a depth $d_2'$ at a point along the second segment 430, wherein the depths $d_1$, $d_2$, $d_1'$, and $d_2'$ are described herein below. The point at which the depth increases from $d_1$ to $d_2$ may occur at any point along the first segment 420. In some embodiments, for example, the point at which the depth increases from $d_1$ to $d_2$ may occur in the first 10%, 20%, 30%, 40%, 50%, 60%, 70%, 80%, or 90% of the groove as measured from the first terminus 422. The point at which the depth increases from $d_1'$ to $d_2'$ may occur at any point along the second segment 430. In some embodiments, for example, the point at which the depth increases from $d_1'$ to $d_2'$ may occur in the first 10%, 20%, 30%, 40%, 50%, 60%, 70%, 80%, or 90% of the groove as measured from the second terminus 432. While FIG. 5E presents depth $d_1$ and depth $d_1'$ as relatively equal, the depth $d_1$ and the depth $d_1'$ may be the same or different. FIG. 5E also presents depth $d_2$ and depth $d_2'$ as relatively equal, but the depth $d_2$ and the depth $d_2'$ may be the same (e.g., with a uniform groove floor therebetween) or different (e.g., with a non-uniform or sloped groove floor therebetween). When the depth $d_1$ and the depth $d_1'$ are the same, when the depth $d_2$ and the depth $d_2'$ are the same, and when the points at which the depth increases from $d_1$ to $d_2$ and from $d_1'$ to $d_2'$ are equidistant from their respective termini (e.g., first terminus 422 for the depth increase from $d_1$ to $d_2$, and second terminus 432 for the depth increase from $d_1'$ to $d_2'$), the groove may have a symmetric depth profile as shown in FIG. 5E. In other embodiments, when the groove has a non-symmetric depth profile, the first segment 420 may be shallower than the second segment 430 providing a better restorative force as described herein. In such other embodiments, each of $d_1'$ and $d_2'$ may individually be equally deep or deeper than $d_1$ and $d_2$, respectively.

Figure 5F:
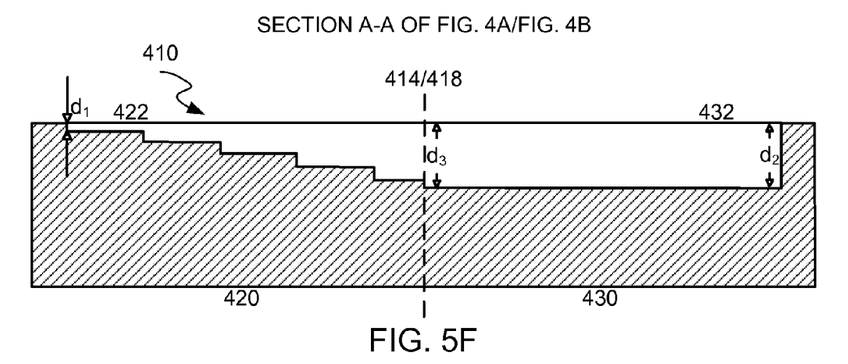

FIG. 5F provides a groove having a non-uniform depth profile when viewed along the length of the groove from the first terminus 422 to the second terminus 432 (see Section A-A in FIGS. 4A, 4B). As shown, the groove may have a depth $d_1$ at the first terminus 422, a series of steps down to a depth $d_3$ at the vertices 414 and 418, and a depth $d_2$ at the second terminus 432, wherein the depths $d_3$ and $d_2$ are optionally equal, and wherein the depths $d_1$, $d_2$, and $d_3$ are described herein below. Each step in the series of steps, from depth $d_1$ at the first terminus 422 to depth $d_3$ at the vertices 414 and 418, may have the same or different dimensions. With respect to having the same dimensions, each step in the series of steps may have the same depth and length. For example, each step in the series of steps may have a point (e.g., midpoint along length and top surface of step) that adheres to a slope determined by depth $d_1$ and depth $d_3$. With respect to having different dimensions, each step in the series of steps may have a different depth and length. For example, the steps near the first terminus 422 may be shallower in depth and longer in length than the steps near the vertices 414 and 418. In an alternative example, the steps near the first terminus 422 may be shallower in depth and shorter in length than the steps near the vertices 414 and 418. The depth of the groove at any point along the second segment 430 of the groove profiled in FIG. 5F may be determined from the slope calculated from the depth $d_2$ at the second terminus 432 and the depth $d_3$ at the vertices 414 and 418. While FIG. 5F presents depth $d_2$ and $d_3$ as relatively equal, the depth $d_2$ and the depth $d_3$ may be the same or different. When the depth $d_2$ and the depth $d_3$ are the same, as shown in FIG. 5F, the groove may have a uniform portion as represented by second segment 430 and a non-uniform portion as represented by first segment 420.

A pressure-generating groove may have a depth profile as described in reference to FIG. 5A, FIG. 5B, FIG. 5C, FIG. 5D, FIG. 5E, and FIG. 5F. A groove may comprise a depth of at least 0.1 µm, 0.5 µm, 1 µm, 2 µm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, or 19 µm at one or more positions along the length of the groove. A groove may comprise a depth of no more than 20 µm, 19 µm, 18 µm, 17 µm, 16 µm, 15 µm, 14 µm, 13 µm, 12 µm, 11 µm, 10 µm, 9 µm, 8 µm, 7 µm, 6 µm, 5 µm, 4 µm, 3 µm, 2 µm, 1 µm, 0.5 µm, or 0.1 µm at one or more positions along the length of the groove. Combinations of the foregoing may also be used to describe the depth of a groove at one or more positions along the length of the groove. For example, a groove may comprise a depth of at least 0.1 µm and no more than 20 µm (i.e., between 0.1 µm and 20 µm) at one or more positions along length of the groove, such as at least 0.5 µm and no more than 10 µm (i.e., between 0.5 µm and 10 µm), for example, at least 1 µm and no more than 5 µm (i.e., between 1 µm and 5 µm).

Figure 6:
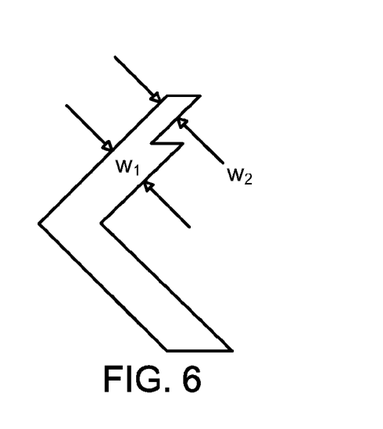
FIG. 6 provides an embodiment of a groove with non-uniform widths.

FIG. 6 provides an embodiment of a pressure-generating groove of a fluid dynamic bearing (e.g., journal bearing, thrust bearing) with non-uniform widths. While the width profile described herein below with reference to FIG. 6 is primarily described with respect to non-uniform width, it should be understood that groove length, groove depth, and certain groove angles may vary as well, as described herein.

FIG. 6 provides a groove having a non-uniform width profile with respect to the first terminus 422 (see FIG. 4A or FIG. 4B). The groove may have a width $w_1$ along a length of first segment 420, which first segment may extend from vertices 414 and 418 to the first terminus 422, and which first terminus is oriented toward an end of a bearing (e.g., top/bottom of journal bearing; circumferential edge of thrust bearing), and the groove may have a width $w_2$ at the first terminus 422 (see FIG. 4A or FIG. 4B), wherein width $w_1 > w_2$. As shown in FIG. 6, the change in width of the groove, from width $w_1$ to width $w_2$, may follow a stepwise reduction; however, the reduction in width of the groove may follow a slope or grade, or a combination of the foregoing. As such, in reducing the width of the groove from $w_1$ to $w_2$, there may be many intermediate widths (e.g., $w_{1.1}$, $w_{1.2}$, $w_{1.3}$ ... $w_2$). The reduction in groove width from $w_1$ to $w_2$ may commence at any point along the length of the first segment 420. In some embodiments, the reduction in groove width commences in the first 5%, 10%, 15%, 20%, 25%, 30%, 35%, 40%, 45%, 50%, 55%, 60%, 65%, 70%, 75%, 80%, 85%, 90%, 95% of the first segment of the groove, as measured from vertices 414 and 418. In some embodiments, the reduction in groove width commences in the first 5%, 10%, 15%, 20%, 25%, 30%, 35%, 40%, 45%, 50%, 55%, 60%, 65%, 70%, 75%, 80%, 85%, 90%, 95% of the first segment of the groove, as measured from the first terminus 422.

Figure 7:
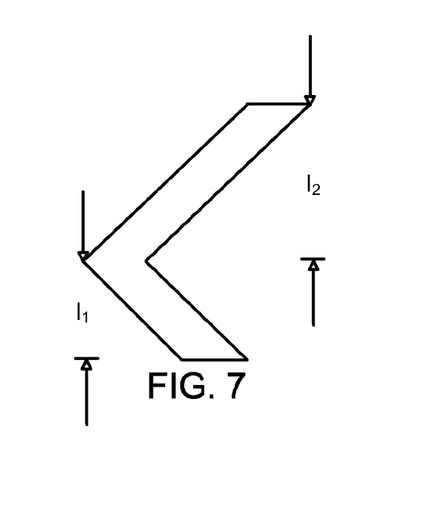
FIG. 7 provides an embodiment of a groove with non-uniform lengths.

FIG. 7 provides an embodiment of a pressure-generating groove of a fluid dynamic bearing (e.g., journal bearing, thrust bearing) with non-uniform lengths. While the length profile described herein below with reference to FIG. 7 is primarily described with respect to non-uniform length, it should be understood that groove width, groove depth, and certain groove angles may vary as well, as described herein.

FIG. 7 provides a groove having a non-uniform length profile with respect to the length of the first segment 420 as compared to the second segment 430 (see FIG. 4A or FIG. 4B). The groove may have a length $l_1$ for first segment 420, which first segment 420 may extend from vertices 414 and 418 to first terminus 422, and the groove may have a length $l_2$ for second segment 430, which second segment 430 may extend from vertices 414 and 418 to second terminus 432, wherein $l_1 > l_2$. In some embodiments, the length $l_1$ of the first segment 420 of a groove may be at least 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95% greater than the length $l_2$ of the second segment 430 of the groove. In some embodiments, the length $l_1$ of the first segment 420 of a groove may be no more than 100%, 95%, 90%, 85%, 80%, 75%, 70%, 65%, 60%, 55%, 50%, 45%, 40%, 35%, 30%, 25%, 20%, 15%, 10%, 5%, 4%, 3%, 2%, or 1% greater than the length $l_2$ of the second segment 430 of the groove. Combinations of the foregoing may also be used to describe the length $l_1$ as compared to the length $l_2$. For example, the length $l_1$ of the first segment 420 of a groove may be at least 0.5% and no more than 100% (i.e., between 0.5% and 100%) greater than the length $l_2$ of the second segment 430 of the groove, such as at least 0.5% and no more than 50% (i.e., between 0.5% and 50%), for example, at least 0.5% and no more than 25% (i.e., between 0.5% and 25%).

Figure 8:
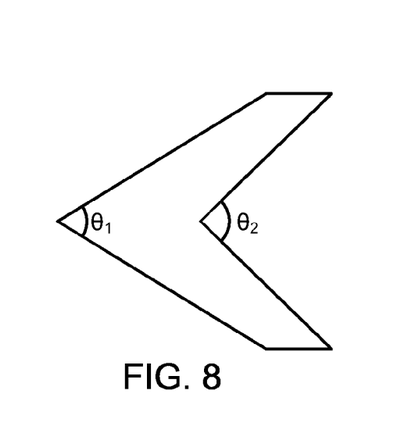
FIG. 8 provides an embodiment of a groove with non-uniform angles.

FIG. 8 provides an embodiment of a pressure-generating groove of a fluid dynamic bearing (e.g., journal bearing, thrust bearing) with non-uniform angles. While the angle profile described herein below with reference to FIG. 8 is primarily described with respect to non-uniform angles, it should be understood that groove width, groove depth, and groove length may vary as well, as described herein.

FIG. 8 provides a groove having a non-uniform angle profile with respect to outside wall vertex 414 as compared to the inside wall vertex 418 (see FIG. 4A or FIG. 4B). The groove may have an angle $\theta_1$ for outside wall vertex 414, and the groove may have an angle $\theta_2$ for inside wall vertex 418, wherein $\theta_1 > \theta_2$. As such, outside wall vertex 414 may be closer to inside wall vertex 418 than when $\theta_1 = \theta_2$. Concomitant with the outside wall vertex 414 being closer to the inside wall vertex 418, the length of outside wall 412 from outside wall vertex 414 to either the first terminus 422 or second terminus 432 may be shorter than the corresponding length of the inside wall 416. As shown in FIG. 8, the groove may have an angle $\theta_1$ for outside wall vertex 414, and the groove may have an angle $\theta_2$ for inside wall vertex 418, wherein $\theta_1 < \theta_2$. As such, outside wall vertex 414 may be farther from inside wall vertex 418 than when $\theta_1 = \theta_2$. Concomitant with the outside wall vertex 414 being farther from the inside wall vertex 418, the length of outside wall 412 from outside wall vertex 414 to either the first terminus 422 or second terminus 432 may be longer than the corresponding length of the inside wall 416. In some embodiments, each of $\theta_1$ and $\theta_2$ may individually measure at least 5°, 10°, 15°, 20°, 25°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, or 175° degrees. In some embodiments, each of $\theta_1$ and $\theta_2$ may individually measure no more than 180°, 175°, 170°, 165°, 160°, 155°, 150°, 145°, 140°, 135°, 130°, 125°, 120°, 115°, 110°, 105°, 100°, 95°, 90°, 85°, 80°, 75°, 70°, 65°, 60°, 55°, 50°, 45°, 40°, 35°, 30°, 25°, 20°, 15°, or 10°. Combinations of the foregoing may also be used to describe each of $\theta_1$ and $\theta_2$. For example, each of $\theta_1$ and $\theta_2$ may individually measure at least 5° and no more than 180° (i.e., between 5° and 180°), such as at least 15° and no more than 165° (i.e., between 15° and 165°, for example at least 30° and no more than 150° (i.e., between 30° and 150°) or at least 45° and no more than 135° (i.e., between 45° and 135°).

FIG. 9 is a plan view of a data storage device in which fluid dynamic bearings (e.g., journal bearings, thrust bearings) described herein may be used. A disk drive 1000 generally includes a base plate 1002 and a cover (not shown) that may be disposed on the base plate 1002 to define an enclosed housing for various disk drive components. The disk drive 1000 includes one or more data storage disks 1004 of computer-readable data storage media. Typically, both of the major surfaces of each data storage disk 1004 include a plurality of concentrically disposed tracks for data storage purposes. Each data storage disk 1004 is mounted on a hub 1006, which in turn is rotatably interconnected with the base plate 1002 and/or cover. Multiple data storage disks 1004 are typically mounted in vertically spaced and parallel relation on the hub 1006. A spindle motor 1008 rotates the data storage disks 1004.

The disk drive 1000 also includes an actuator arm assembly 1010 that pivots about a pivot bearing 1012, which in turn is rotatably supported by the base plate 1002 and/or cover. The actuator arm assembly 1010 includes one or more individual rigid actuator arms 1014 that extend out from near the pivot bearing 1012. Multiple actuator arms 1014 are typically disposed in vertically spaced relation, with one actuator arm 1014 being provided for each major data storage surface of each data storage disk 1004 of the disk drive 1000. Other types of actuator arm assembly configurations could be utilized as well, an example being an "E" block having one or more rigid actuator arm tips, or the like, that cantilever from a common structure. Movement of the actuator arm assembly 1010 is provided by an actuator arm drive assembly, such as a voice coil motor 1016 or the like. The voice coil motor 1016 is a magnetic assembly that controls the operation of the actuator arm assembly 1010 under the direction of control electronics 1018.

A load beam or suspension 1020 is attached to the free end of each actuator arm 1014 and cantilevers therefrom. Typically, the suspension 1020 is biased generally toward its corresponding data storage disk 1004 by a spring-like force. A slider 1022 is disposed at or near the free end of each suspension 1020. What is commonly referred to as the read/write head (e.g., transducer) is appropriately mounted as a head unit (not shown) under the slider 1022 and is used in disk drive read/write operations. The head unit under the slider 1022 may utilize various types of read sensor technologies such as anisotropic magnetoresistive (AMR), giant magnetoresistive (GMR), tunneling magnetoresistive (TuMR), other magnetoresistive technologies, or other suitable technologies.

The head unit under the slider 1022 is connected to a preamplifier 1026, which is interconnected with the control electronics 1018 of the disk drive 1000 by a flex cable 1028 that is typically mounted on the actuator arm assembly 1010. Signals are exchanged between the head unit and its corresponding data storage disk 1004 for disk drive read/write operations. In this regard, the voice coil motor 1016 is utilized to pivot the actuator arm assembly 1010 to simultaneously move the slider 1022 along a path 1030 and across the corresponding data storage disk 1004 to position the head unit at the appropriate position on the data storage disk 1004 for disk drive read/write operations.

When the disk drive 1000 is not in operation, the actuator arm assembly 1010 is pivoted to a "parked position" to dispose each slider 1022 generally at or beyond a perimeter of its corresponding data storage disk 1004, but in any case in vertically spaced relation to its corresponding data storage disk 1004. In this regard, the disk drive 1000 includes a ramp assembly 1032 that is disposed beyond a perimeter of the data storage disk 1004 to both move the corresponding slider 1022 vertically away from its corresponding data storage disk 1004 and to also exert somewhat of a retaining force on the actuator arm assembly 1010.

Thus, provided herein is an apparatus, comprising a journal bearing comprising a sleeve and a shaft configured for a fluid therebetween, wherein the journal bearing comprises a set of upper journal bearing grooves and a set of lower journal bearing grooves, and wherein each set of grooves comprises a plurality of chevron-shaped grooves, each chevron-shaped groove comprising at least two of a non-uniform depth, non-uniform angle, a non-uniform width, or a non-uniform length, selected to provide a predetermined spindle-motor stiffness to the journal bearing during steady-state operation and during a shock event. In some embodiments, each chevron-shaped groove includes an outside wall, the vertex of which points to an adjacent chevron-shaped groove, and an inside wall, the vertex of which points to the outside wall of the same chevron-shaped groove. In some embodiments, the non-uniform depth includes the outside wall of each chevron-shaped groove being deeper than the inside wall. In some embodiments, the non-uniform depth includes the inside wall of each chevron-shaped groove being deeper than the outside wall. In some embodiments, the non-uniform depth includes a center groove of each chevron-shaped groove being deeper than both the outside wall and the inside wall. In some embodiments, the non-uniform angle includes the vertex of the outside wall of each chevron-shaped groove being a narrower angle than the vertex of the inside wall. In some embodiments, the set of upper journal bearing grooves and the set of lower journal bearing grooves are the same. In some embodiments, the set of upper journal bearing grooves and the set of lower journal bearing grooves are different. In some embodiments, the sleeve includes both sets of journal bearing grooves. In some embodiments, the shaft includes both sets of journal bearing grooves.

Also provided herein is an apparatus, comprising a thrust bearing comprising a thrust surface and an opposing surface configured for a fluid therebetween, wherein the thrust bearing comprises a set of thrust bearing grooves, and wherein the set of thrust bearing grooves comprises a plurality of chevron-shaped grooves, each chevron-shaped groove comprising a symmetric depth profile selected to provide a predetermined spindle-motor stiffness during steady-state operation and during operation at a temperature higher than an optimum temperature range. In some embodiments, the optimum temperature range is between about 35° C. and 45° C. In some embodiments, each chevron-shaped groove includes an outside wall, the vertex of which points to an adjacent chevron-shaped groove, and an inside wall, the vertex of which points to the outside wall of the same chevron-shaped groove. In some embodiments, the symmetric depth profile includes a center groove of each chevron-shaped groove being deeper than both the inside wall and outside wall of the groove. In some embodiments, the center includes an angled bottom or a flat bottom. In some embodiments, the thrust surface includes the set of thrust bearing grooves. In some embodiments, the opposing surface includes the set of thrust bearing grooves.

Also provided herein is an apparatus, comprising a fluid dynamic bearing, wherein the fluid dynamic bearing comprises a set of pressure-generating grooves, and wherein the set of pressure-generating grooves comprises a plurality of chevron-shaped grooves, each chevron-shaped groove comprising at least two selected from a non-uniform depth, non-uniform angle, a non-uniform width, or a non-uniform length, selected to provide a predetermined spindle-motor stiffness to the journal bearing during steady-state operation and during a shock event. In some embodiments, each chevron-shaped groove comprises a non-uniform depth and at least one selected from a non-uniform angle, a non-uniform width, or a non-uniform length. In some embodiments, each chevron-shaped groove includes a first segment, from the vertex of the chevron-shaped groove to a first terminus, oriented toward an end of the fluid dynamic bearing, and a second segment, from the vertex of the chevron-shaped groove to a second terminus, oriented toward the center of the fluid dynamic bearing. In some embodiments, the non-uniform width includes the first terminus of each chevron-shaped groove being narrower than the second terminus. In some embodiments, the non-uniform length includes the first segment of each chevron-shaped groove being longer than the second segment.

While the invention has been described and/or illustrated by means of various embodiments and/or examples, and while these embodiments and/or examples have been described in considerable detail, it is not the intention of the applicant(s) to restrict or in any way limit the scope of the invention to such detail. Additional adaptations and/or modifications of the invention may readily appear to persons having ordinary skill in the art to which the invention pertains, and, in its broader aspects, the invention may encompass these adaptations and/or modifications. Accordingly, departures may be made from the foregoing embodiments and/or examples without departing from the scope of the invention, which scope is limited only by the following claims when appropriately construed.

What is claimed is:

1. An apparatus, comprising:
a fluid dynamic bearing,
wherein the fluid dynamic bearing comprises a set of pressure-generating grooves, and
wherein the set of pressure-generating grooves comprises a plurality of chevron-shaped grooves, each chevron-shaped groove comprising at least two characteristics selected from a non-uniform depth, a non-uniform angle, a non-uniform width, or a non-uniform length, selected to provide a predetermined spindle-motor stiffness to the fluid dynamic bearing during steady-state operation and during a shock event.

2. The apparatus of claim 1, wherein the fluid dynamic bearing comprises
a journal bearing comprising a sleeve and a shaft configured for a fluid therebetween,
wherein the set of pressure-generating grooves comprises a set of upper journal bearing grooves and a set of lower journal bearing grooves.

3. The apparatus of claim 2, wherein each chevron-shaped groove comprises an outside wall, the vertex of which points to an adjacent chevron-shaped groove, and an inside wall, the vertex of which points to the outside wall of the same chevron-shaped groove.

4. The apparatus of claim 3, wherein the non-uniform depth comprises the outside wall of each chevron-shaped groove being deeper than the inside wall.

5. The apparatus of claim 3, wherein the non-uniform depth comprises the inside wall of each chevron-shaped groove being deeper than the outside wall.

6. The apparatus of claim 3, wherein the non-uniform depth comprises a center groove of each chevron-shaped groove being deeper than both the outside wall and the inside wall.

7. The apparatus of claim 3, wherein the non-uniform angle comprises the vertex of the outside wall of each chevron-shaped groove being a narrower angle than the vertex of the inside wall.

8. The apparatus of claim 2, wherein the set of upper journal bearing grooves and the set of lower journal bearing grooves are the same.

9. The apparatus of claim 2, wherein the sleeve comprises both sets of journal bearing grooves.

10. The apparatus of claim 2, wherein the shaft comprises both sets of journal bearing grooves.

11. The apparatus of claim 1, wherein the fluid dynamic bearing comprises
a thrust bearing comprising a thrust surface and an opposing surface configured for a fluid therebetween,
wherein the set of pressure-generating grooves comprises a set of thrust bearing grooves.

12. The apparatus of claim 11, wherein each chevron-shaped groove comprises an outside wall, the vertex of which points to an adjacent chevron-shaped groove, and an inside wall, the vertex of which points to the outside wall of the same chevron-shaped groove.

13. The apparatus of claim 12, wherein each chevron-shaped groove comprises a symmetric depth profile selected to provide a predetermined spindle-motor stiffness during steady-state operation and during operation at a temperature higher than an optimum temperature range, wherein the symmetric depth profile comprises a center groove of each chevron-shaped groove of the set of thrust bearing grooves being deeper than both the inside wall and outside wall of the groove.

14. The apparatus of claim 13, wherein the optimum temperature range is between about 35° C. and 45° C.

15. The apparatus of claim 13, wherein the center comprises an angled bottom or a flat bottom.

16. The apparatus of claim 11, wherein the thrust surface comprises the set of thrust bearing grooves.

17. The apparatus of claim 11, wherein the opposing surface comprises the set of thrust bearing grooves.

18. The apparatus of claim 1, wherein each chevron-shaped groove comprises a non-uniform depth and at least one characteristic selected from a non-uniform angle, a non-uniform width, or a non-uniform length.

19. The apparatus of claim 18, wherein each chevron-shaped groove comprises a first segment, from the vertex of the chevron-shaped groove to a first terminus, oriented toward an end of the fluid dynamic bearing, and a second segment, from the vertex of the chevron-shaped groove to a second terminus, oriented toward the center of the fluid dynamic bearing, and wherein the non-uniform width comprises the first terminus of each chevron-shaped groove being narrower than the second terminus.

20. The apparatus of claim 18, wherein each chevron-shaped groove comprises a first segment, from the vertex of the chevron-shaped groove to a first terminus, oriented toward an end of the fluid dynamic bearing, and a second segment, from the vertex of the chevron-shaped groove to a second terminus, oriented toward the center of the fluid dynamic bearing, and wherein the non-uniform length comprises the first segment of each chevron-shaped groove being longer than the second segment.

21. An apparatus, comprising:
a fluid dynamic bearing,
wherein the fluid dynamic bearing comprises a set of pressure-generating grooves, and
wherein the set of pressure-generating grooves comprises a plurality of chevron-shaped grooves, each chevron-shaped groove comprising at least two characteristics selected from the group consisting of a non-uniform depth, a non-uniform angle, a non-uniform width, and a non-uniform length, selected to provide a predetermined spindle-motor stiffness to the fluid dynamic bearing during steady-state operation and during a shock event.

22. The apparatus of claim 21, wherein each chevron-shaped groove comprises a non-uniform depth and at least one characteristic selected from the group consisting of a non-uniform angle, a non-uniform width, and a non-uniform length, wherein each chevron-shaped groove comprises a first segment, from the vertex of the chevron-shaped groove to a first terminus, oriented toward an end of the fluid dynamic bearing, and a second segment, from the vertex of the chevron-shaped groove to a second terminus, oriented toward the center of the fluid dynamic bearing, and wherein the non-uniform width comprises the first terminus of each chevron-shaped groove being narrower than the second terminus.

* * * * *